(12) United States Patent
Henderson et al.

(10) Patent No.: US 6,863,906 B2
(45) Date of Patent: *Mar. 8, 2005

(54) L-ERGOTHIONEINE, MILK THISTLE, AND S-ADENOSYLMETHIONINE FOR THE PREVENTION, TREATMENT AND REPAIR OF LIVER DAMAGE

(75) Inventors: Todd R. Henderson, Jarrettsville, MD (US); Barbara E. Corson, Fawn Grove, PA (US)

(73) Assignee: Nutramax Laboratories, Inc., Edgewood, MD (US)

(*) Notice: Subject to any disclaimer, the term of this patent is extended or adjusted under 35 U.S.C. 154(b) by 213 days.

This patent is subject to a terminal disclaimer.

(21) Appl. No.: 10/153,877

(22) Filed: May 24, 2002

(65) Prior Publication Data

US 2002/0198169 A1 Dec. 26, 2002

Related U.S. Application Data

(63) Continuation of application No. 09/731,719, filed on Dec. 8, 2000, now abandoned, which is a continuation-in-part of application No. 09/256,352, filed on Feb. 24, 1999, now Pat. No. 6,555,141.
(60) Provisional application No. 60/076,347, filed on Feb. 27, 1998.

(51) Int. Cl.[7] ............................................. A61K 35/78
(52) U.S. Cl. ...................... 424/725; 514/46; 514/398; 514/399
(58) Field of Search ......................... 424/725; 514/46, 514/398, 399

(56) References Cited

U.S. PATENT DOCUMENTS

| | | | |
|---|---|---|---|
| 3,882,228 A | 5/1975 | Boncey et al. | |
| 3,887,700 A | 6/1975 | Boncey et al. | |
| 4,061,765 A | 12/1977 | Madaus et al. | |
| 4,100,160 A | 7/1978 | Walser | |
| 4,296,127 A | 10/1981 | Walser | |
| 4,314,989 A | 2/1982 | Rosen | |
| 4,994,457 A | 2/1991 | Crawford et al. | |
| 5,084,482 A | 1/1992 | Hirsch et al. | |
| 5,137,712 A | 8/1992 | Kask et al. | |
| 5,288,503 A | 2/1994 | Wood et al. | |
| 5,474,757 A | 12/1995 | Yang | |
| 5,569,458 A | 10/1996 | Greenberg | |
| 6,255,295 B1 | 7/2001 | Henderson et al. | |
| 6,271,213 B1 | 8/2001 | Henderson et al. | |
| 6,555,141 B1 | 4/2003 | Corson et al. | |
| 6,583,123 B2 | 6/2003 | Henderson et al. | |

OTHER PUBLICATIONS

Adachi et al., "The Effects of S–adenosylmethionine on Intrahepatic Cholestatis," Jpn. Arch. Int. Med., 33(6): 185–192 (1986).

(List continued on next page.)

*Primary Examiner*—Francisco Prats
(74) *Attorney, Agent, or Firm*—Covington & Burling (57) ABSTRACT

This invention provides therapeutic compositions and combinations for the protection, treatment and repair of liver tissue. The invention relates to novel compositions and combinations comprising two or more compounds selected from the group consisting of S-adenosylmethionine, L-ergothioneine, and a substance selected from the group consisting of constituents of Milk thistle (*Silybum marianum*), silymarin and active components of silymarin, whether naturally, synthetically, or semi-synthetically derived, and to methods of preventing and treating liver disease and of repairing damaged liver tissue. The invention also provides a method of administering these compositions and combinations to humans or animals in need thereof.

49 Claims, 6 Drawing Sheets

S-ADENOSYLMETHIONINE

OTHER PUBLICATIONS

Akanmu, D. et al., "The Antioxidant Action of Ergothioneine," Archives of Biochemistry and Biophyiscs, 288(1): 10–16 (1991).

Alvaro, D. et al., S–adenosylmethionine (SAMe) protects against acute ethanol hepatotoxicity in the isolated perfused rat liver (IPRL) with no effect on trascytosis, EASL, Journal of Hepatology, 21(Suppl. 1): S81 (1994).

Arias, I.M. and Kinne, R., On the pathophysiology and reversibility of intrahepatic cholestasis, Clinical Research, 32:548A (1984).

Aruoma O.I. et al., "Antioxidant action of ergothioneine: assessment of its ability to scavenge peroxynitrite," Biochem. Biophys. Res. Commun. 231(2): 389–91, abstract (Feb. 13, 1997).

Baldessarini, R., "Neuropharmacology of S–Adenyosyl–L–Methionine," American Journal of Medicine, 83(5A): 95–103 (1987).

Barrio, E. et al., Comparative effect of nifedipine and s–adenosylmethionine, singly and in combination on experimental rat liver cirrhosis, Life Sciences, 52:PL 217–220 (1993).

Belli, D.C. et al., S–adenosylmethionine prevents total parenteral nutrition–induced cholestasis in the rat, Journal of Hepatology, 21: 18–23 (1994).

Bortolini, M. et al., Multicentre Survey of the Prevalence of Intrahepatic Cholestasis in 2520 Consecutive Patients with Newly Diagnosed Chronic Liver Disease, Drug Investigation, 4(Suppl. 4): 83–89 (1992).

Botero, R.C., Placebo controlled trial of intravenous S–Adenosylmethionine (SAMe) in patients with acute hepatitis A, B, and NANB, Hepatology, 14(4):199A (1991).

Bray, G.P. et al., A comparison of S–Adenosylmethionine (SAMe), rifampicin (R) and ursodeoxycholic acid (UDCA) in primary biliary cirrhosis (PBC): interim results, Journal of Hepatology, 13(Suppl. 2):S101 (1991).

Bray, G.P. et al., Resolution for danazol–induced cholestasis with S–Adenosylmethionine, Postgrad. Med. J., 69:237–239 (1993).

Bray, G.P., et al., S–Adenosylmethionine Protects against Acetaminophen Hepatotoxicity in Two Mouse Models, Hepatology, 15(2): 297–301 (1992).

Brown, M.D. et al., s–Adenosyl–L–methionine modulates $Na^+ + K^+$–ATPase activity in rat colonic basolateral membranes, Biochem. J., 251:215–222 (1988).

Brummel, M.C., "In Search of a Physiological Function for L–ergothioneine,–II," Med. Hypotheses, 30(1):39–48 (Sep. 1989).

Buchet, J–P. et al., The influence of liver disease on the methylation of arsenile in humans. Archives of Toxicology, 55: 151–154 (1984).

Caballeria, E. and Moreno, J., Therapeutic effects of S–Adenosylmethionine (SAMe) in hepatic steatosis, A pilot study, Acta Therapeutica, 16: 253–264 (1990).

Caballeria, J. et al., Effects of S–adenosylmethionine (SAMe) on experimental liver fibrosis. In: Falk symposium 71. Fat–storing Cells and Liver Fibrosis, Surrenti, C. et al. (Eds.) Kluwer Academic Publishers, Lancaster, UK, 314–321 (1994).

Cacciatore, L. et al., S–Adenosylmethionine (SAMe) in the treatment of pruritus in chronic liver disease, Acta Therapeutica, 15: 363–371 (1989).

Carney, M., Neuropharmacology of S–Adenosyl Methionine, Clinical Neuropharmacology, 9(3): 235–243 (1986).

Casini, A. et al., S–Adenosylmethionine Inhibits Collagen Synthesis by Human Fibroblast In Vitro, Meth. and Find. Exp. Clin. Pharmacol., 11(5):331–334 (1989).

Champe, P., Biochemistry, 2nd Edition, J.B. Lippincott Co., Philadelphia, 1994, pp. 248, 250 and 265.

Chawla, R.K. et al., Effect of Ethanol Consumption on Metabolism of S–Adenosyl–L–Methionine in Rat Liver, Drug Investigation, 4 (Suppl. 4): 41–45 (1992).

Chawla, R.K. and Jones, D.P., "Abnormal metabolism of S–adenosyl–L–methionine in hypoxic rat liver. Similarities to its abnormal metabolism in alcholic cirrhosis," Biochimia et Biophysica Acta, 1199: 45–51 (1994).

Cibin, M. et al., S–Adenosylmethionine (SAMe) is effective in reducing ethanol abuse in an outpatient program for alcoholics, Biochmeical and social aspects of alcohol and alcoholism, Kuriyama, K. et al. (eds.) Elsevier Science Publishers B.V. (Biomedical Division), 357–360 (1988).

Concari, M. et al., S–adenosyl–L–methionine (SAMe) reduces hepatotoxicity induced by hydrophobic bile salts (BS) in hepG2 cell line, EASL, Journal of Hepatology, 21(Suppl. 1):S77 (1994).

Conti, M. et al., Protective Activity of Silipide on Liver Damage in Rodents, Japan J. Pharmacol., 60:315–21 (1992).

Corrales, F. et al., S–adenosylmethionine Treatment Prevents Carbon Tetracholoride–induced S–adenosylmethionine Synthetase Inactivation and Attenuates Liver Injury, Hepatology, 16(4):1022–1027 (1992).

Cuomo, R. et al., Bile and biliary lipid secretion in rats with hexachlorobenzene–induced prophyria. Effect of S–adenosyl–L–methionine administration, Journal of Hepatology, 12: 87–93 (1991).

Cuomo, R. et al., Nicotinamide methylation in patients with cirrhosis, Journal of Hepatology, 20: 138–142 (1994).

Cuomo, R. et al., S–Adenosyl–L–Methionine (SAMe)–dependent nicotinamide methylation: a marker of hepatic damage, In: Falk Symposium 71–Fat Storing Cells and Liver Fibrosis, Surrenti, C. et al. (Eds.), Kluwer Academic Publishers, Lancaster, UK, 348–353 (1994).

Cutrin, C. et al., Effect of nifedipine and S–Adenosylmethionine in the liver of rats treated with $CCl_4$ and ethanol for one month, Life Sciences, 51:PL 113–118 (1992).

Cutrin, C. et al., Lactacidaemia in rats with cirrhosis induced by carbon tetrachloride and ethanol: treatment with colchicine, nifedipine and S–adenosylmethionine, Med. Sci. Res., 19:351–352 (1991).

Dausch et al., "Increased Levels of S–Adenosylmethionine in the Livers of Rats Fed Various Forms of Selenium," Nutrition and Cancer, 20 (1) 31–39–(1993).

Devi, B.G. et al., Effect of Ethanol on Rat Fetal Hepatocytes: Studies on Cell Replication, Lipid Peroxidation and Glutathione, Hepatology, 18(3):648–659 (1993).

Devi, B. et al., Protection of rat fetal hepatocytes membranes from ethanol mediated cell injury and growth impairment, Hepatology, 16: 109A (1992).

Di Padova, C. et al., Decreased Blood Levels of Ethanol and Acetaldehyde by S–Adenosyl–L–Methionine in Humans, Disease, Metabolism, and Reproduction in the Toxic Response to Drugs and Other Chemicals, Arch. of Toxicol., Suppl. 7: 240–242 (1984).

Di Padova, D. et al., S–Adenosyl–L–Methionine protection against α–naphthyl–isothlocyanate–induced cholestasis in the rat, Toxicology Letters, 29:131–136 (1985).

Dunne, B. et al., S–adenosylmethionine improves hepatic function during liver perfusion after sequential cold and warm ischaemic injury. Submitted to: British Transplant Society (1992).

Dunne, B. et al., Benefit of S–adenosylmethionine After Sequential Cold and Warm Hepatic Ischaemia is Derived from Three Separate Treatment Stages, EASL, Journal of Hepatology, 18(Suppl 1):S66 (1993).

Dunne, B. et al., S–Adenosylmethionine and N–Acetylcysteine in the treatment of experimental ischaemic liver injury, Journal of Hepatology, 16(Suppl. 1):S46 (1992).

Dunne, J.B. et al., Donor pretreatment is essential for maximal benefit of S–Adenosylmethionine in reducing experimental hepatic ischaemic injury, Hepatology, 18(4):64A (1993).

Dunne, J.B. et al., Evidence that S–adenosylmethionine and N–Acetylcysteine reduce in injury from sequential cold and warm ischaemia in the isolated perfused rat liver, Transplanation, 57(8): 1161–1168 (1994).

Fell, D. and Steele R.D., Effect of Retinol Toxicity on Hepatic S–Adenosylmethionine–Dependent Transmethylation in Rats, Drug–Nutrient Interactions, 5: 1–7 (1987).

Feo et al., "Early stimulation of polyamine biosynthesis during promotion by phenobarbital of diethylnitrosamine–induced rat liver carcinogenesis. The effects of variations of the S–adenosyl–L–methionine cellular pool," Carcinogenesis, 6(12): 1713–20 (1985).

Feo, F. et al., Effect of the Variations of S–Adenosyl–L–methionine Liver Content on Fat Accumulation and Ethanol Metabolism in Ethanol–Intoxicated Rats. Toxicology and Applied Pharmacology, 83:331–341 (1986).

Feo, F. et al., The role of Phosphatidylethanolamine Methylation in the Synthesis of Phosphatidylcholine in Acute Ethanol Intoxication, Research Communications, in Substances of Abuse, 3(4):499–502 (1982).

Feo, F. et al., "The Variations of S–Adenosyl–L–methionine Content modulate hepatocyte growth during phenobarbital promotion of diethylnitrosamine–induced rat liver carcinogenesis," Toxicologic Pathology, 15(1): 109–114 (1987).

Fernandez, E. et al., Cyclosporin A–Induced Cholestasis in the Rat. Beneficial effects of S–Adenosyl–L–Methionine, Drug Investigation, 4(Supl. 4):54–63 (1992).

Fischer, G. et al., S–Adenosylmethionine (SAMe) does not restore microsomal function in rats with secondary biliary cirrhosis (SBC) but improves transsulphuration, Journal of Hepatology, 16:S71 (1992).

Foster, S., A Field Guide to Medicinal Plants, Houghton Miffing Co., Boston, 198 (1990).

Frezza, M. et al., "Oral S–adenosylmethionine in the Symptomatic Treatment of Intrahepatic Cholestasis," Gastroenterology, 99: 211–215 (1990).

Frezza, M. and Terpin, M., "The Use of S–Adenosyl–L–Methionine in the Treatment of Cholestatic Disorders," Drug Investigation, 4 (Suppl. 4): 101–08 (1992).

Garcea, R. et al., "Inhibition of promotion and persistent nodule growth by S–Adenosyl–L–methionine in rat liver carcinogenesis: role of remodeling and apoptosis," Cancer Research, 49: 1850–1856 (1989).

Garcea, R. et al., "Variations of ornithine decarboxylase activity and S–adenosyl–L–methionine and 5'–methylthioadenosine'contents during the development of diethylnitrosarmine–induced liver hyperplastic nodules and hepatocellular carcinoma," Carcinogenesis, 8(5): 653–58 (1987).

Gasso M. et al., Influence of S–adenosylmethionine (SAMe) on lipid peroxidation and liver fibrogenesis in CC14–induce cirrhosis, EASL, Journal of Hepatology, 21(Suppl. 1):S3 (1994).

Gentile, S. et al., Age–associated decline of hepatic handling of cholephillic anions in humans is reverted by S–adenosylmethionine (SAMe), Scand. J. Clin. Lab. Invest., 50:565–571 (1990).

Gentile, S. et al., Effect of different doses of s–adenosyl–L–methionine (SAMe) on nicotinic acid–induced hyperbilirubinaemia in Gilbert's syndrome, Scand. J. Clin. Lab. Invest., 48:525–529 (1988).

Geubel, A.P. et al., Abnormal methylation capacity in human liver cirrhosis, Int. J. Clin. Pharm. Res. VIII(2): 117–122 (1988).

Giannuoli, G. et al. S–Adenosylmethionine for treatment of pruritus in compensated chronic liver disease. A pilot study, Hepatology, 6(5):1110 (1986).

Giulidori, P. et al., "Transmethylation, transsulfuration and aminopropylation reaction of S–adenosyl–L–methionine in vivo," J. Biol. Chem. 259&):4205–4211 (1984).

Gonzalez–Gallego, J. et al., Pretreatment of rats with S–Adenosyl–L–Methionine (SAMe) prevents exercise–induced cholestasis, Journal of Hepatology, 16(Suppl. 1):S93 (1992).

Hanlon, D., "Interaction of Ergothioneine with Metal Ions and Metalloenzymes," J. Med. Chem., 14(11): 1084–87 (1971).

Hartman, Phillip E., "Ergothioneine as Antioxidant," Methods in Enzymology, 186: 310–318, Academic Press, Inc. (1990).

Iemmolo, R.M. et al., Intrahepatic Cholestasis in Biliary Cirrhois Secondary to Graft Versus Host Disease (GVHD): Report of a Case Treated with Ademetionine (SAMe), Journal of Hepatology, 18(Suppl. 1):S132 (1993).

Israël, Y. et al., Metabolism of hepatic glutathione and its relevance in alcohol induced liver damage. In: Cellular and Molecular Aspects of Cirrhoiss. Clement, B. and Guillouzo, A. (Eds.) Colloque INSERM/John Libbey Eurotext Ltd, 216:25–37 (1992).

Janicak, P.G. et al., "S–Adenosylmethionine in Depression," Alabama Journal of Medical Sciences, 25(3): 306–313 (1988).

Jimenez, R. et al., Effect of Acute Preadministration of Sulfoadenysyl–L–Methionine (SAMe) on the Hepatotoxicity of Cyclosporine A., Hepatology, 16:268A (1992).

Kakimoto, H. et al., Changes in lipid composition of erthrocyte membranes with administration of S–adenosyl–L–methionine in chronic liver disease, Gastroenterologia Japonica, 27(4): 508–513 (1992).

Kawano, H. et al., "Studies on Ergothioneine. XI.1) Inhibitory Effect on Lipid Peroxide Formation in Mouse Liver," Chem. Pharm. Bull. 31(5): 1682–1687 (1983).

Kaye et al., "Metabolism of Exogenous S–Adenosyl–L–Methionine in Patients with Liver Disease," Drugs, 40 (Sup. 3): 124–138 (1990).

Laffi, G. et al., Plasma membrane abnormalities in chronic liver disease. In: Cholestasis, Gentilini, P. et al., (Eds.) Elsevier Science B.V. Amsterdam, 205–212 (1994).

Lieber, C.S., Alcohol and the liver, In: Falk Symposium 71—Fat–Storing Cells and Liver Fibrosis, Surrenti, C. et al. (Eds.) Kluwer Academic Publishers, Lancaster UK, 135–166 (1994).

Lieber, C.S. Alcoholic liver injury, Current Opinion in Gastroenterology, 8: 449–457 (1992).

Lieber, C.S., Biochemical Factors in Alcoholic Liver Disease, Seminars in Liver Disease, 13(2): 136–153 (1993).

Lieber, C.S., Hepatotoxicity of Alcohol. Implications for the Therapy of Alcoholic Liver Disease, Drug Investigation, 4(Supp. 4): 1–7 (1992).

Lieber, C.S. and Decarli, L.M., Hepatotoxicity of ethanol. Journal of Hepatology, 12:394–401 (1991).

Lieber, C.S. et al., S–Adenosyl–L–methionine attenuates alcohol–induced liver injury in the baboon. Hepatology, 11: 165–172 (1990).

Loguerico, C. et al., Effects of S–adenosyl–L–methionine administration on red blood cell cysteine and glutathione levels of alcoholic patients with and without liver disease, Alcohol & Alcoholism, 29(5): 597–604 (1994).

Lucas, R. et al., Ability of S–adenosyl–L–methionine (SAMe) to antagonize cyclosporine A–induced inhibition of the billiary excretion of glutathione, EASL, Journal of Hepatology, 21 (Suppl.1):S87 (1994).

Manzillo, G. et al., Multicentre Double–Blind Placebo–Controlled Study of Intravenous and Oral S–Adenosyl–L–Methionine (SAMe) in Cholestatic Patients with Liver Disease, Drug Investigation, 4:(Suppl. 4): 90–100 (1992).

Mascio, G. et al., Intramuscular (IM) and intravenous (IV) S–Adenosylmethionine 1,4 butanedisulfonate (SAMe SD4) for the symptomatic treatment of intrahepatic cholestasis (IHC). Results of a placebo–controlled study, The Italian Journal of Gastroenerology, 23(5):314–315 (1991).

Muriel, P. and Mourelle, M., Characterization of membrane fraction lipid composition and function of cirrhotic rat liver. Role of S–adenosyl–L–methionine, Journal of Hepatology, 14: 16–21 (1992).

Muriel, P. and Mourelle, M., Prevention and reversion of erythrocyte membrane alterations in cirrhosis by S–adenosylmethionine, Hepatology, 10(4):742 (1989).

Muriel, P. et al., Protective effect of S–adenosyl–l–methionine on liver damage induced by biliary obstruction in rats: a histological, ultrastructural and biochemical approach, Journal of Hepatology, 21, 95–102 (1994).

Nanno, T. et al., Effect of S–adenosyl–L–methionine (SAMe) on experimental intrahepatic cholestasis, Proc. Jpn. Soc. Clin. Metabl., 24 (1987).

Osada, J. et al., Effects of S–adenosyl–L–methionine on phospholipid methyltransferase activity changes induced by thioacetamide, Biochemical Pharmacology, 40: 648–651 (1990).

Osada, J. et al., Effect of S–Adenosyl–L–Methionine on thioacetamide–induced liver damage in rats, Toxicology Ltters, 32:97–106 (1986).

Owen J.S. et al., Ability of S–Adenosyl–L–Methionine to Ameliorate Lipoprotein–Induced Membrane Lipid Abnormalities and Cellular Dysfunctions in Human Liver Disease, Drug Investigation, 4(Suppl. 4): 22–40 (1992).

Owen, J.S. et al., Decreased erythrocyte membrane fluidity and altered lipid composition in human liver disease, Journal of Lipid Research, 23: 124–132 (1982).

Par. A., "Pathogenesis and Management of Alcoholic Liver Injury," Acta Physiologica Hungarcia, 80 (1–4): 325–350 (Jan. 1992).

Paredes, S. R. et al., S–Adenosyl–L–Methionine: Its Effect on Minolevulinate Dehydratase and Glutahione in Acute Ethanol Intoxication. Alcohol. 4:81–85 (1987).

Parish, R. et al., Treatment of Amanita Mushroom Poisoning: A Review, Vet. Hum. Toxocol., 28(4): 318–22 (1986).

Pascale, R. et al., Inhibition by Ethanol of Rat Liver Plasma Membrane Na+K+) ATPase: Protective Effect of S–Adenosyl–L–Methionine, L–methionine, and N–acetylcysteine, Toxicology and Applied Pharmacology, 97: 216–229 (1989).

Pascale, R. et al., "The Role of S–Adenosylmethionine in the Regulation of Glutathione Pool and Acetaldehyde Production in Acute Ethanol Intoxication," Research Communications in Substances of Abuse, 5(4): 321–24 (1984).

Perisco, M. et al., The association between rifamycin–SV (R–SV) related hyperbilirubinaemia and antipyrine clearance as a new test of liver function in cirrhois, European Journal of Clinical Investigation, 24: 201–204 (1994).

Persico, M. et al., S–Adenosylmethionine (SAMe)—induce improvement of hepatic handling of organic anions in cirrhosis, Gastroenterology, 98:A620 (1990).

Piccinino, F. et al., S–Adenosyl–Methionine in patients with chronic active hepatitis treated with steroids, Italian Journal of Gastroenterology, 14: 186–187 (1982).

Plasenica, A.M.C. et al., Total Parenteral Nutrition Plus S–Adenosylmethionine in a Case of Intrahepatic Cholestasis, Drug Invest., 3(5):333–335 (1991).

Ponsoda, X. et al., Intracellular glutathione in human hepatocytes incubated with S–Adenosyl–L–methionine and GSH–depleting drugs, Toxicology, 70:293–302 (1991).

Rafique, S. et al., Reversal of extrahepatic membrane cholesterol deposition in patients with chronic liver diseases by S–adenosyl–L–methionine, Clinical Science, 83: 353–356 (1992).

Rafique, S. et al., S–Adenosyl–L–Methionine (SAMe) in the Treatment of Benign Recurrent Intraheptic Cholestasis (BRIC), European Journal of Clinical Investigation, 21(2):30 (1991).

Roda, E. et al., Effects of ademetionine (SAMe)and UDCA on bile acid metabolism and bile acid pool size in primary biliary cirrhosis, In: Falk Symposium 71—Fat–Storing Cells and Liver Fibrosis, Surrenti, C. et al., (Eds.), Kluwer Academic Publishers, Lancaster, UK, 354–360 (1994).

Roda, E. et al., Effect of oral Ademetionine (SAMe) on bile acid (BA) metabolism in primary biliary cirrhosis (PBC), European Journal of clinical investigation, 22(4):A19 (1992).

Schenker, S. and Halff, G.A., Nutritional therapy in alcoholic liver disease, Seminars in Liver Disease, 13(2): 196–209 (1993).

Schreiber, A.J. et al, Enhancement of taurocholate secretory maximum: S–Adenosyl Methionine (SAMe)–induced cytoprotection, Clinical Research, 31(1):86A (1983).

Schreiber, A.J. et al., S–Adenosyl Methionine (SAMe)–induced cytoprotection against bile acid–induced cholestasis, Gastroenterology, 84:1395 (1983).

Scott, P.D. et al., S–Adenosyl–L–Methionine Protects against Haemorrhagic Pancreatitis in Partially Immunosuppressed Pancreaticoduodenal Transplant Recipients, Drug Investigation, 4(Suppl. 4):69–77 (1992).

Seyoum, G. and Persaud, T.V.N., In vitro effect of s–adenosyl methionine on ethanol embryopathy in the rat, Exp. Toxic Pathol., 46: 177–181 (1994).

Stramentinoli, G., Modulation of membrane fluidity by S–adenosylmethionine treatment in different experimental conditions. In: 1st Conference on Biochemical Pharmacological and Clinical Aspects of Transmethylation, Mato, J.M. (Editor), Jarpyo Editores, Madrid, 97–104 (1986).

Stramentinoli, G., "Pharmacologic aspects of S–adenosylmethionine. Pharmacokinetics and pharmacodynamics," Am. J. Med., 83(5A): 35–42 (1987).

Stramentinoli, G. et al., Protective role of S–Adenosyl–Methionine against acetaminophen induced mortality and hepatotoxicity in mice, Biochemical Pharmacology, 28, 3567–3571 (1979).

Stramentinoli, G. et al., Protective role of S–Adenosyl–L–Methionine on liver injury induced by D–Galactosamine in rats, Biochemical Pharmacology, 27:1431–1433 (1978).

Thorn, H. et al., Anti–Ischaemic Activity of S–Adenosyl–L–Methionine (SAMe) during Hypoxia/Reoxygenation in the Isolated Perfused Rat Liver, Drug Investigation, 4(Suppl. 4):64–68 (1992).

Tsuji, M. et al., Protective effect of S–Adenosyl–L–Methionine against $CCl_4$ –Induced Hepatotoxity in Cultured Hepatocytes, Japan. J. of Pharmacol., 52:209–214 (1990).

Tsuji, M et al., Protective effects of S–Adenosyl–L–Methionine against enzyme leakage from cultured hepatocytes and hypotonic hemolysis, Japanese Journal of Pharmacology, 52:45–49 (1990).

Tyler, V., The Honest Herbal, Haworth Press, Inc., New York, 209–10 (1993).

Vara, E. et al., S–Adenosyl–L–Methionine Might Protect Transplanted Hepatocytes Against the Toxic Effects of Cytokines, Transplantation Proceedings, 26(6): 3363–3365.

Vendmiale et al., Effects of Oral S–Adenosyl–L–Methionine on Hepatic Glutathione in Patients with Lvier Disease, Scand. J. Gastroenterol., 24: 407–415 (1989).

Vendemiale, G. et al., S–Adenosylmethionine (SAMe) improves acetaminophen metabolism in cirrhotic patients, Journal of Hepatology, 9(Suppl. 1):S240 (1989).

Villa, J.G. et al., Impairment of Bile Secretion Induced by Exhaustive Exercise in the Rat, Int. J. Sports Med., 14: 179–184 (1983).

Vogel, Guenter, et al., Protection by Silibinin against Aminita phalliodes Intoxicant in Beagles. Toxicology and Applied Pharmacology, 73: 355–362 (1948).

Wichtl, M. (Grainger Bisset, N, trans.), Herbal Drugs and Phytopharmaceuticals, CRC press, Boca Raton, 121–125 (1994).

Musso, A. et al., "Considerationi sull'uso della Silimarina e della SAMe net trattamento dell'epatite infettiva acuta dell'infanzia," Minerva Pediatrica, 32(17): 1057–1067 (1980), with English translation.

The Merck Index. Badavari et al., editors. pp. 1350–1351 (1989).

Kawano et al., Chem. Pharm. Bull. 31(5): 1682–1687 (1983).

S-ADENOSYLMETHIONINE

FIG.1

L-ERGOTHIONEINE

FIG. 3 BIOCHEMICAL FACTORS IN ALCOHOLIC LIVER DISEASE

SILYBIN

SILYCHRISTIN

SILYDIANIN

TAXIFOLIN
2,3-DIHYDROQUERCETIN

FIG. 7

L-ERGOTHIONEINE, MILK THISTLE, AND S-ADENOSYLMETHIONINE FOR THE PREVENTION, TREATMENT AND REPAIR OF LIVER DAMAGE

CROSS-REFERENCE TO RELATED APPLICATIONS

The present application is a continuation-in-part application of U.S. patent application Ser. No. 09/256,352, filed Feb. 24, 1999, the disclosure of which is hereby incorporated by reference herein in its entirety. That application claimed priority to provisional application: "L-ERGOTHIONEINE, MILK THISTLE, AND S-ADENOSYLMETHIONINE FOR LIVER FAILURE," U.S. Ser. No. 60/076,347, filed Feb. 27, 1998, the disclosure of which is hereby incorporated by reference herein in its entirety.

FIELD OF THE INVENTION

The present invention relates to compositions and combinations for the protection, treatment and repair of liver tissues in humans and animals.

BACKGROUND OF THE INVENTION

The liver is an extremely important organ. As the major metabolic organ of the body, the liver plays some role in almost every biochemical process, including the deamination of amino acids and the formation of urea, the regulation of blood sugar through the formation of glycogen, the production of plasma proteins, the production and secretion of bile, phagocytosis of particulate matter from the splanchnic (intestinal) circulation, and the detoxification and elimination of both endogenous and exogenous toxins.

The many functions of the liver depend on its intimate association with circulating blood. Each liver cell is exposed on at least one face to a blood sinusoid which contains oxygenated arterial blood mixed with venous blood from the splanchnic circulation. This profuse blood supply is necessary for the liver to function. The blood from the sinusoids supplies the hepatocytes with oxygen and nutrients. The hepatocytes use the nutrients both for their own metabolic needs and for the synthesis of the liver's many essential products. Abnormalities in the blood or vasculature can have immediate and severe effects on the liver. For example, liver cells are exposed to high concentrations of any toxic compounds that are ingested orally, such as ethyl alcohol. Even when the ingested compound is not itself toxic, intermediate derivatives produced during hepatic metabolism of the compound may damage the hepatocytes. This phenomenon occurs, for example, in carbon tetrachloride poisoning. Since the blood moves slowly through hepatic sinusoids, liver cells are also quite vulnerable to blood-borne infectious agents such as viruses and bacteria. Furthermore, derangements in hepatic blood pressure can damage liver tissue. Right-sided cardiac failure increases hepatic blood pressure and can lead to pressure necrosis (hepatocellular death) and fibrosis. Left-sided cardiac failure can reduce hepatic perfusion and lead to hepatocellular anoxia and death.

Liver damage from any source may result in liver regeneration, necrosis (cell death), degeneration, inflammation, fibrosis, or mixtures of these processes, depending on the type and extent of injury and its location within the liver. The liver has great functional reserves, but with progressive injury, disruption of liver function can have life-threatening consequences. Cirrhosis, which is a type of end-stage liver disease, is one of the top ten causes of death in the Western world.

Despite the significance and potential severity of liver disease, therapeutic approaches are limited. Treatment is generally symptomatic, e.g., the use of diuretics to combat tissue edema caused by low levels of plasma proteins. Many types of liver disease are the result of viruses (e.g., hepatitis A, B, C, D and E, to name a few), and effective antiviral therapies are rare and commonly cause potentially severe side effects. Other liver diseases are the result of previous toxic exposure (such as alcoholic cirrhosis and exposure to toxic plants, or environmental pollutants) which may be difficult to control. In still other cases, liver disease is the result of poorly understood interplay of various factors, including genetic factors, environmental conditions, and immune system activity (autoimmune hepatitis). These cases are, in a word, idiopathic, and as such are difficult to treat except symptomatically. In short, due in part to the complexity of liver disease, therapies do not currently exist that address its causes. Nor does there currently exist a therapy that supports normal liver function and helps heal damaged liver tissue. Currently available therapies either focus only on the secondary symptoms of liver disease or have significant side effects, as is the case with antiviral drugs. There is a need for a therapeutic composition that will support liver structure, function and healing, with few or no side effects.

SUMMARY OF THE INVENTION

The present invention provides compositions and combinations for the protection, treatment and repair of liver tissue in humans and animals.

Additionally, the present invention provides such compositions and combinations that also produce a low level of side effects.

The present invention also provides a method of using the novel compositions and combinations of the present invention to protect, treat or repair liver tissue in humans or animals in need thereof.

The present invention provides novel compositions, combinations and methods for protecting, treating and repairing liver tissue. The compositions and combinations of the invention include two or more of the following compounds: S-adenosylmethionine, L-ergothioneine and a substance selected from the group consisting of a constituent of Milk thistle, silymarin and active components of silymarin, whether naturally, synthetically, or semi-synthetically derived.

DETAILED DESCRIPTION OF THE INVENTION

In accordance with the teachings of the present invention, disclosed herein are compositions, combinations and methods for the protection, treatment and repair of liver tissue. The invention relates to novel compositions and combinations comprising two or more compounds selected from the group consisting of S-adenosylmethionine, L-ergothioneine, and a substance selected from the group consisting of constituents of Milk thistle (*Silybum marianum*), silymarin and active components of silymarin, whether naturally, synthetically, or semi-synthetically derived, and to methods of preventing and treating liver disease and of repairing damaged liver tissue.

Figure 1:
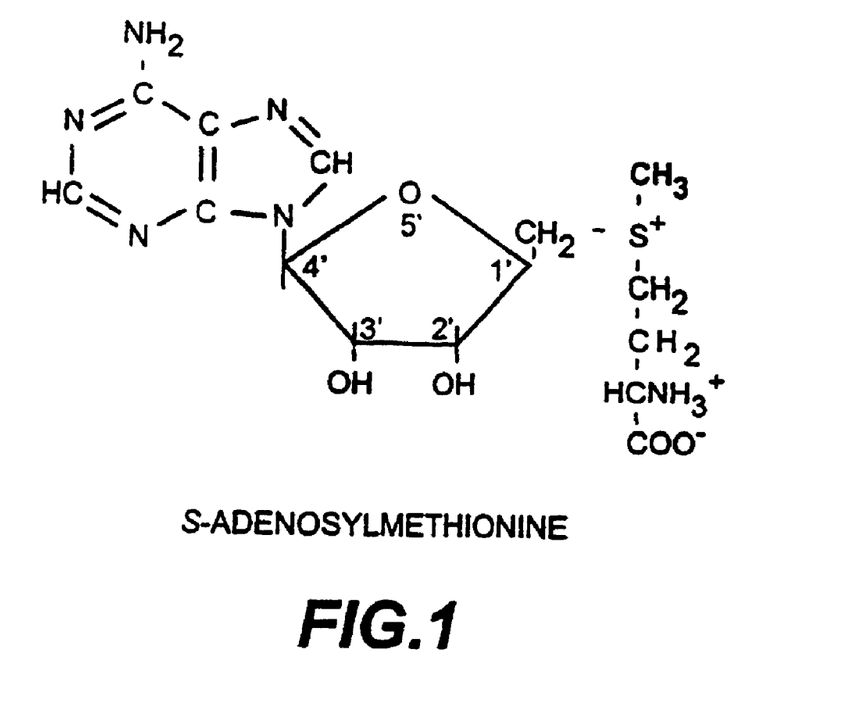
FIG. 1 is the molecular structure of S-adenosylmethionine.
Figure 2:
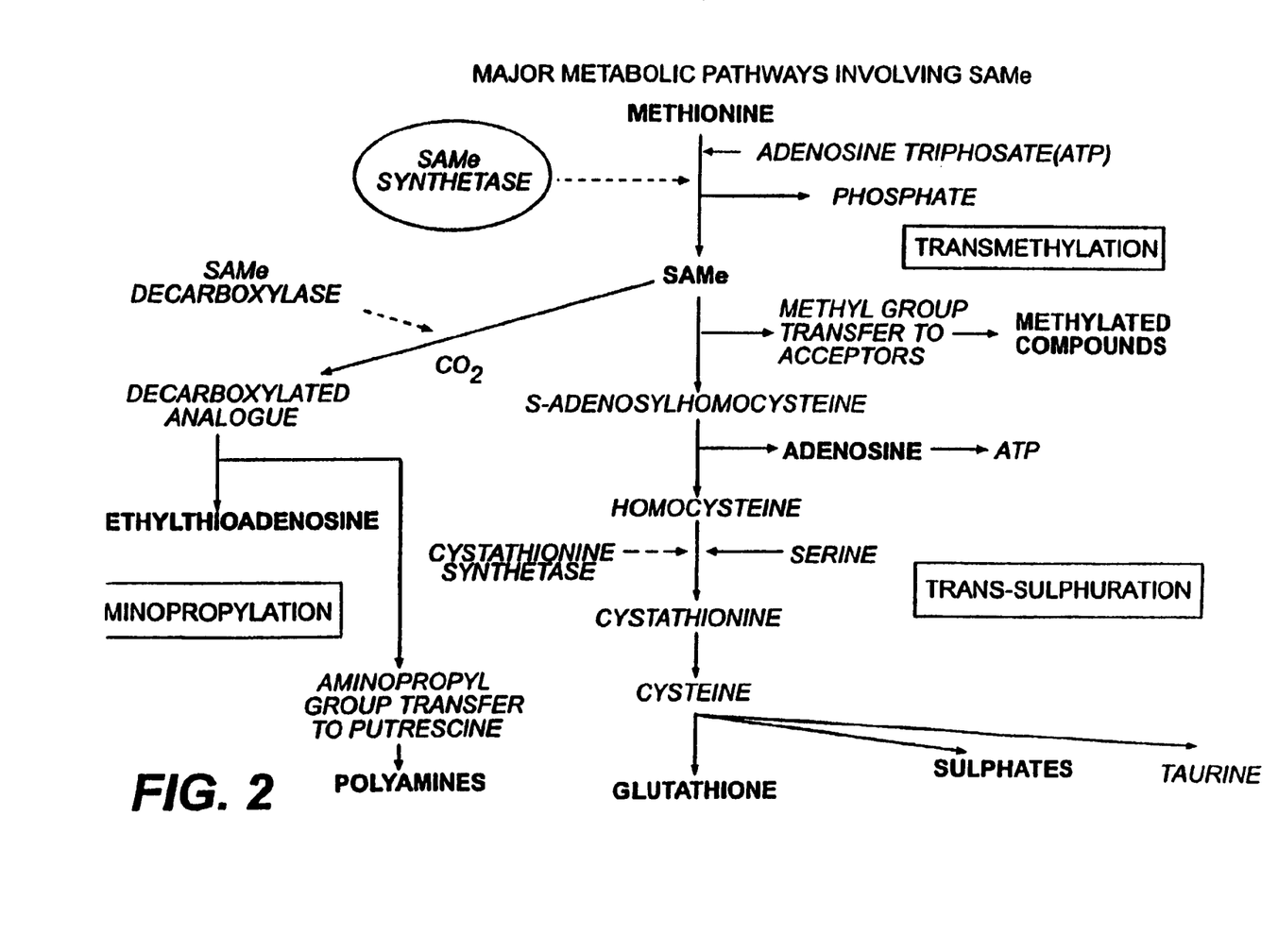
FIG. 2 diagrams the major metabolic pathways of S-adenosylmethionine in the body.

S-adenosylmethionine ("SAMe") (FIG. 1) is a significant physiologic compound that is present throughout body tissue and that takes part in a number of biologic reactions as a methyl group donor or an enzymatic activator during the synthesis and metabolism of hormones, neurotransmitters, nucleic acids, phospholipids, and proteins. It is naturally formed in the body from ATP and methionine. SAMe is an extremely important reactant in many biochemical reactions including transmethylation, transsulfation, and synthesis of amines (FIG. 2). Stramentinoli, G., *Pharmacologic Aspects of S-Adenosylmethionine*, American Journal of Medicine 83 (5A), 1987, pp. 35–42. In higher organisms, SAMe plays a significant role in transmethylation processes in more than 40 anabolic or catabolic reactions involving the transfer of the methyl group of SAMe to substrates such as nucleic acids, proteins and lipids, among others. The release of the methyl group from SAMe is also the start of a "transsulfuration" pathway that produces all endogenous sulfur compounds. After donating its methyl group, SAMe is converted into S-adenosylhomocysteine, which in turn is hydrolyzed to adenosine and homocysteine. The amino acid cysteine may then be produced from the homocysteine. Cysteine may exert a reducing effect by itself or as an active part of glutathione, which is a main cell antioxidant. Id. SAMe additionally has anti-oxidant effects via its derivatives (e.g., methylthioadenosine), which prevent oxidative damage to cells. Glutathione itself is a product of SAMe via the transmethylation and transsulfation pathways.

SAMe and its products, including glutathione, are of great importance in the prevention of liver damage. The changes produced by ethanol (EtOH) in the liver provide examples of injuries that can occur in the liver on the cellular level (FIG. 3), and help explain the mechanism of action by which SAMe counteracts these injuries.

Figure 3:
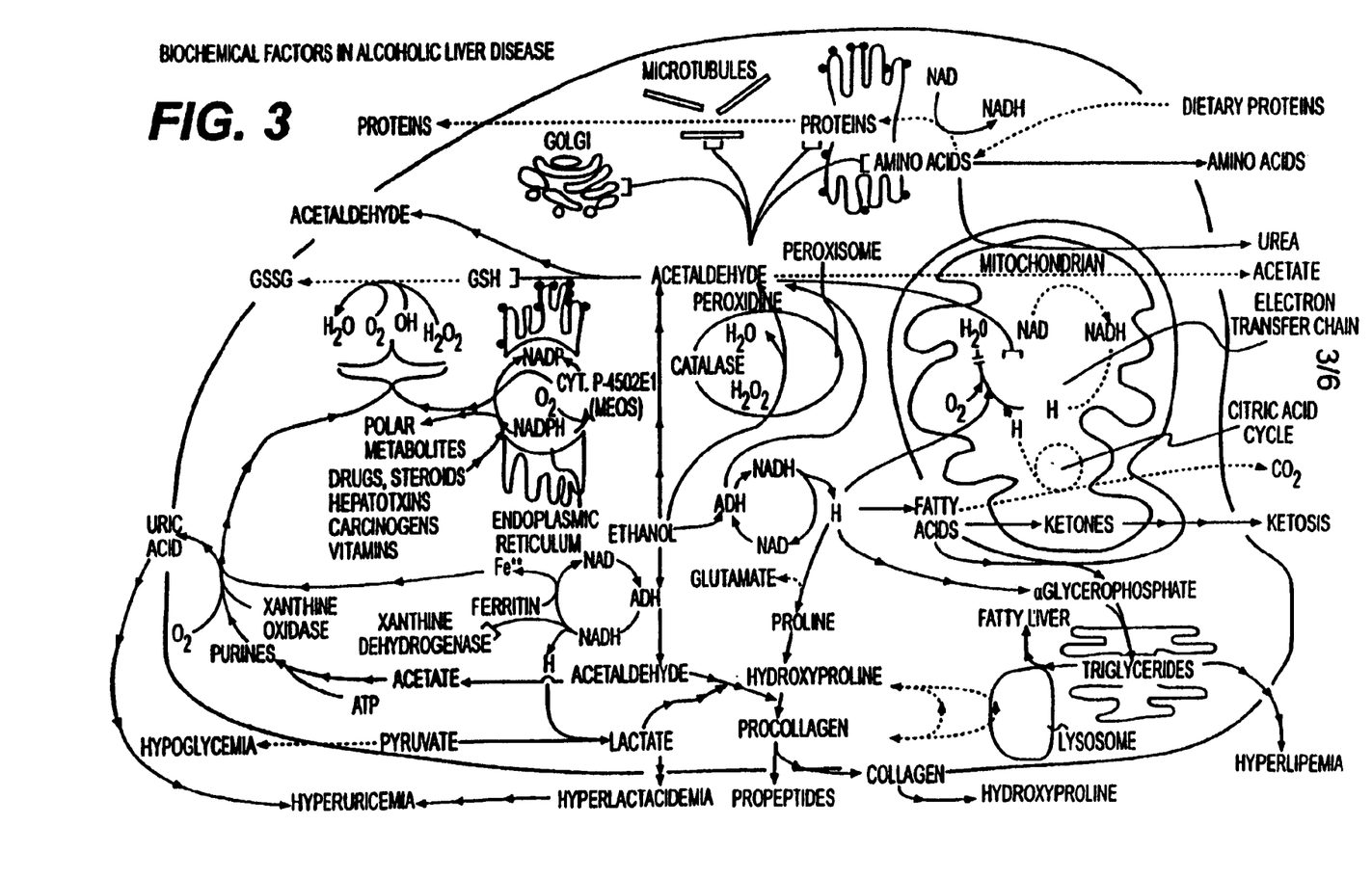
FIG. 3 diagrams the effects of ethanol in the hepatocyte.

EtOH absorbed in the blood stream is metabolized in the liver by the enzyme alcohol dehydrogenase. This reaction releases excess nicotinamide-adenine-dinucleotide (NADH) which in turn shunts substrates (carbohydrates, lipids, and proteins) in the liver away from normal catabolic processes and towards lipid biosynthesis. As lipids accumulate in the liver cells in the form of large droplets, organelles are physically displaced and crowded, and this phenomenon decreases the cells' ability to function. Secondly, alcohol induces the P 450 system of cytochromes, and the microsomal ethanol oxidizing system ("MEOS") within liver cells, leading to augmented transformation of various compounds in the body (including, for example, chemicals from tobacco smoke) into toxic metabolites, and producing free radicals. Because alcohol consumption decreases glutathione pools, damage already produced by these free radicals is exacerbated. Alcohol and its metabolites (e.g., acetaldehyde) also interact with phospholipids and therefore have direct effects on hepatocellular membranes, decreasing their fluidity and affecting the function of organelles such as mitochondria and endoplasmic reticulum. Finally, acetaldehyde alters hepatocellular proteins, including the sodium/potassium pump, decreasing the ability of these proteins to function. The sodium/potassium pump is a membrane-bound protein that is responsible for maintaining the balance of sodium and potassium across the cell membrane of every cell in the body. Because many cell functions depend on the electrochemical gradient that results from this distribution of sodium and potassium, the sodium/potassium pump is essential to enable cells to perform. Liver cells are no exception. The alterations in proteins that alcohol and its metabolites induce also have the effect of making these proteins more 'foreign' and thus more likely to induce autoimmune reactions. In short, alcohol damages the liver in a myriad of ways. FIG. 3; Lieber, C., *Biochemical factors in alcoholic liver disease*, Seminars in Liver Disease, 13 (2), 1993, pp. 136–53.

SAMe has a variety of beneficial effects in cells and protects hepatocytes from these injurious influences in a number of different ways. For example, SAMe has been shown to decrease lipid accumulation in rats chronically intoxicated with ethanol. This effect is not completely understood, but is partially explained by SAMe's ability to inhibit alcohol dehydrogenase. This single function of SAMe in itself prevents not only lipid accumulation but also much of the additional damage acetaldehyde causes to cellular membranes and proteins. Pascale, R., et al., *Inhibition by ethanol of rat liver plasma membrane (Na+K+) ATPase: protective effect of SAMe, L-methionine, and N-acetylcysteine*, Toxicology and Applied Pharmacology, 97, 1989, pp. 216–29. Furthermore, because SAMe catalyses the transformation of phosphatidylethanolamine to phosphatidylcholine, it supports the normal fluidity of cell membranes, thereby supporting the structure and function of organelles including the plasma membrane, mitochondria and endoplasmic reticulum. This supportive effect avoids many of alcohol's damaging secondary effects. Bevi B., et al., *Protection of rat fetal hepatocytes membranes from ethanol mediated cell injury and growth impairment*, Hepatology 16, 1992, p. 109A.

SAMe also protects liver cells indirectly via its antioxidant products cysteine and glutathione, which help prevent damage by the excessive free radicals produced during alcohol intoxication. Pascale R., et al., *The role of SAMe in the regulation of glutathione pool and acetaldehyde production in acute ethanol intoxication*, Research Communications in Substances of Abuse, Vol. 5, No. 4, 1984, pp. 321–24.

Laboratory animal studies and in vitro experiments have verified these effects of SAMe on the inner, lipid layer of the plasma membrane. Champ, P. and Harvey, R., Biochemistry, $2^{nd}$ ed., Lippincott, Philadelphia, 1994, pp. 266–7; Stramentinoli, G., *Pharmacologic aspects of SAMe*, American Journal of Medicine, Vol. 83 (5A) 1987, p. 35; Baldessarini, F., *Neuropharmacology of S-Adenosyl Methionine*, American Journal of Medicine 83 (5A), 1987, p. 95; Carney, M., *Neuropharmacology of S-Adenosyl Methionine*, Clinical Neuropharmacology 9 (3), 1986, p. 235; Janicak, P., *S-Adenosylmethionine in Depression*, Alabama Journal of Medical Sciences 25 (3), 1988, p. 306.

SAMe has been used to treat various disorders. In certain forms of liver disease, SAMe acts as an anticholestatic agent. Adachi, Y., et al., *The Effects of S-adenosylmethionine on Intrahepatic Cholestasis*, Japan Arch. Inter. Med., 33 (6), 1986, pp. 185–92. One mechanism by which SAMe exerts this effect is via its ability to maximize membrane fluidity, which is a crucial factor in the secretion of bile acids from hepatocytes. Id. Another mechanism is via the transsulfation pathway and the production of sulfates and taurine, which are important in mobilization of bile acids. Frezza, M., *The*

*use of SAMe in the treatment of cholestatic disorders*, Drug Investigation, 4 (Suppl. 4), 1992, pp. 101–08. Low levels of SAMe are believed to play a role in increasing the risk of certain cancers. Feo F., et al., *Early Stimulation of Polyamine Biosynthesis During Promotion by Phenobarbital of Diethylnitrosamine-induced Rat Liver Carcinogenesis. The Effects of Variations of the S-adenosyl-L-methionine Cellular Pool*, Carcinogenesis, 6 (12), 1985, pp. 1713–20. The administration of SAMe has also been associated with a fall in the amount of early reversible nodules and the prevention of the development of late pre-neoplastic lesions and hepatocellular carcinomas. Garcea, R., et al., *Variations of Ornithine Decarboxylase Activity and S-adenosyl-L-methionine and 5'-methylthioadenosine Contents During the Development of Diethylnitrosamine-induced Liver Hyperplastic Nodules and Hepatocellular Carcinoma*, Carcinogenesis, 8 (5), 1987, pp. 653–58. SAMe is available in many different salt forms as would be known by a person of ordinary skill in the art, any of which, or any combination of which, would be useful in the invention. SAMe and its salt forms may be natural, semisynthetic, bioengineered, synthetic or extracted, any of which, or any combination of which, would be useful in the invention.

Figure 4:
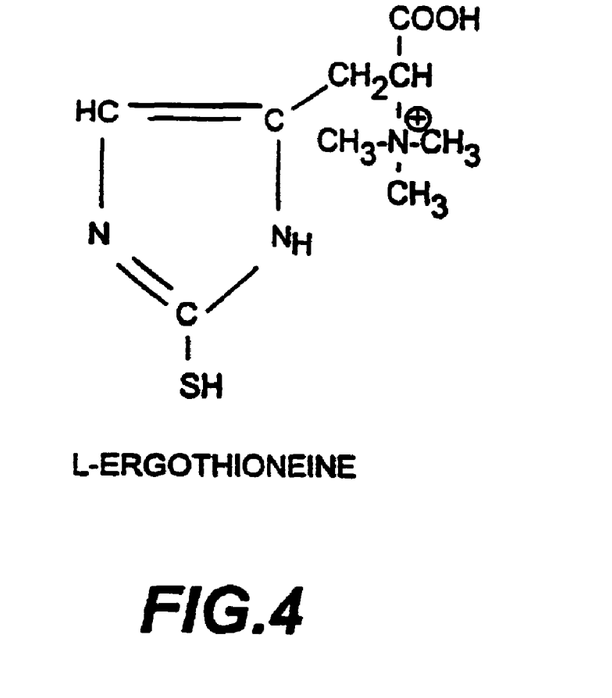
FIG. 4 is the molecular structure of L-ergothioneine.
Figure 5:
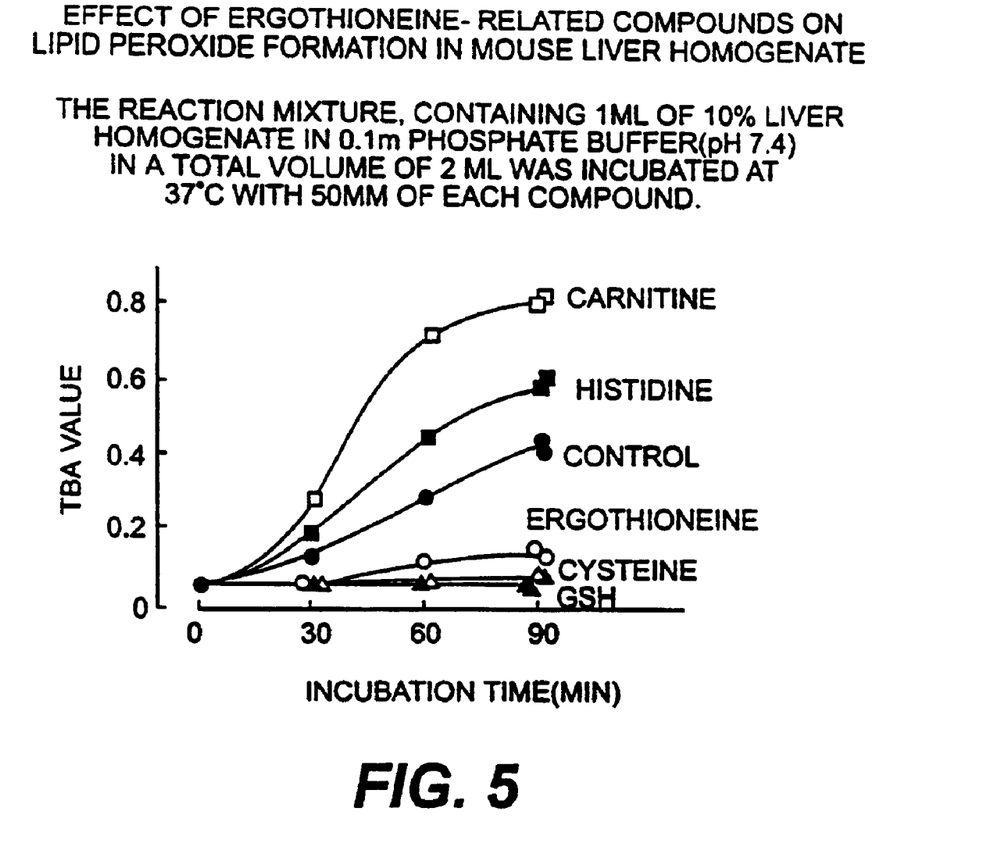
FIG. 5 shows the effect of ergothioneine and other compounds on lipid peroxide formation in mouse liver homogenate.

L-ergothioneine (FIG. 4) is a naturally occurring antioxidant that is very stable in the body. It is synthesized in fungi and microorganisms and present in both plants and animals. Animals are unable to synthesize L-ergothioneine and must obtain it from dietary sources. It is readily absorbed and is active in most mammalian tissues, concentrating especially in the liver, where it prevents certain types of free-radical-induced damage to cell membranes and organelles. For example, exogenous L-ergothioneine has been shown to prevent lipid peroxidation by toxic compounds in the liver tissue of rats. Akanmu, D., et al., *The antioxidant action of ergothioneine*, Arch. of Biochemistry and Biophysics, 288 (1), 1991, pp. 10–16; Kawano, H., et al., *Studies on Ergothioneine: Inhibitory effect on lipid peroxide formation in mouse liver*, Chem. Pharm. Bull., 31 (5), 1983, pp. 1662–87. In a study comparing the inhibition of lipid peroxide ("LPO") formation by various compounds in mouse liver, L-ergothioneine both inhibited LPO formation and enhanced the decomposition of existing LPO (FIG. 5). Id. L-ergothioneine additionally has been shown to inhibit the damaging effects caused by the oxidation of iron-containing compounds, such as hemoglobin and myoglobin. These molecules are important in the body as carriers of oxygen, but because they contain divalent iron, they can interact with hydrogen peroxide via the Fenton reaction to produce the even more damaging hydroxyl radical. This is the mechanism by which damage occurs during so-called reperfusion injury. Because L-ergothioneine acts as a reducing agent of the ferryl-myoglobin molecule, it can protect tissues from reperfusion injury. Hanlon, D., *Interaction of ergothioneine with metal ions and metalloenzymes*, J. Med. Chem., 14 (11), 1971, pp. 1084–87. Although L-ergothioneine does not directly scavenge superoxide anion or hydrogen peroxide, it contributes to the control of these free radicals by participating in the activation of superoxide dismutase and glutathione peroxidase. Its protective effects on cell membranes and other organelles are of benefit in acute and chronic toxicity as well as in infectious diseases, because common pathogenic biomechanisms are active in both of these processes. Ergothionine in any form would be useful in the invention, including natural, semisynthetic, bioengineered, synthetic, extracted and combinations thereof and including any other active forms, such as racemic mixtures (D & L forms). Because ergothioneine is available in nature, it is expected that daily microgram amounts will be effective as an antioxidant. Other antioxidants, such as selenium, are known to be effective as antioxidants at these very low levels.

Figure 6:
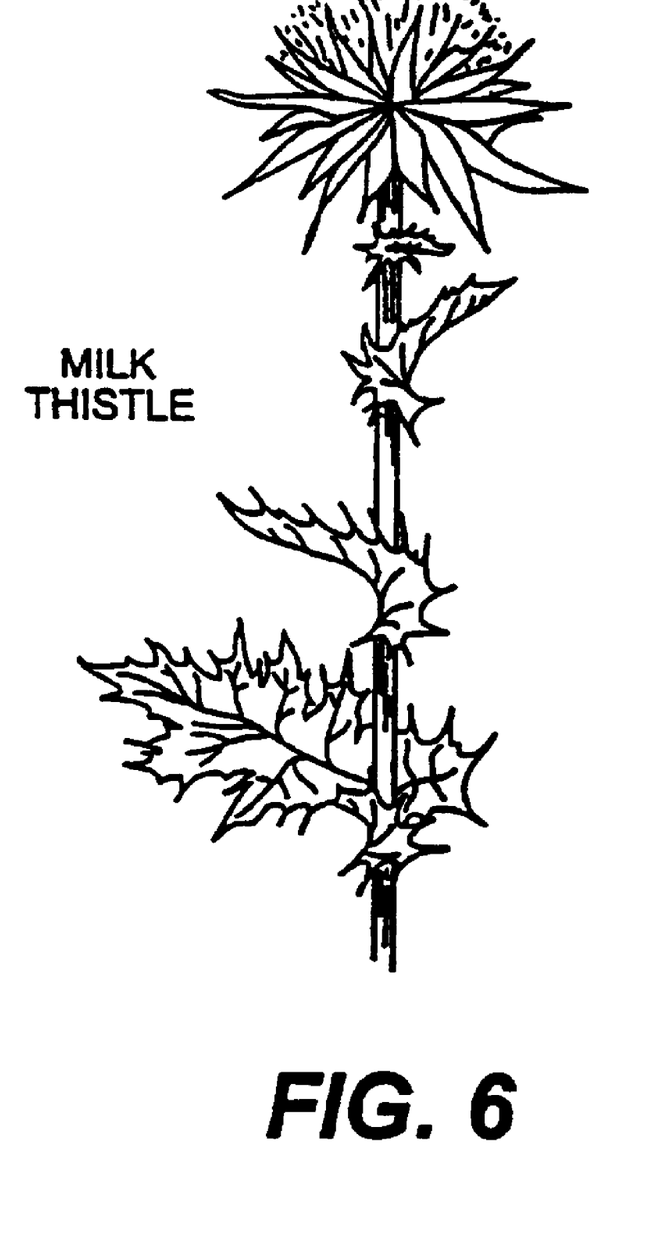
FIG. 6 is a drawing of the herb Milk thistle (*Silybum marianun*).
Figure 7:
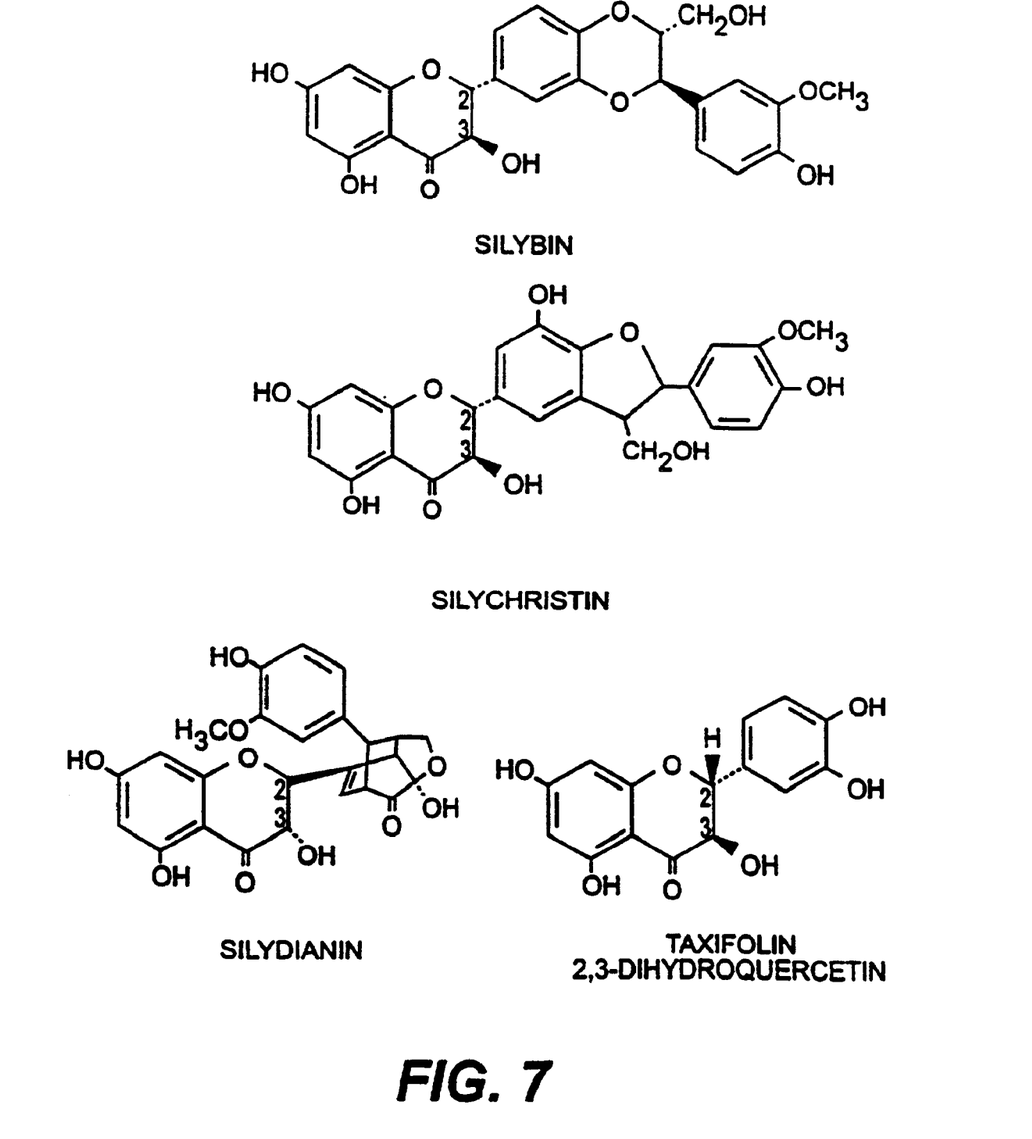
FIG. 7 is the molecular structures of silybin and other compounds from Milk thistle.

Milk thistle (*Silybum marianum*) (FIG. 6), which is also commonly known as Marian thistle, St. Mary's thistle, and Our Lady's thistle, is a native to the Mediterranean region, but has been naturalized in California and the eastern United States. This tall herb with prickly variegated leaves and milky sap has been used as a folk remedy for liver and biliary complaints for many years and recent research has supported such medicinal use. Foster, S., A Field Guide to Medicinal Plants, Houghton Mifflin Co, Boston, 1990, p. 198. Research over the past 20 years has documented that the plant contains a compound referred to as silymarin, which actually consists of various forms of hepatoprotectant flavonolignans. The principal components are silybin (which is also called silybinin); silychristin; and silydianin (which is also called silymonin); the 3-deoxy-derivatives of silychristin and silydianin; as well as isosilychristin; isosilybin (which is also known as isosilybinin) and its 3-deoxy derivative silandrin; the 3-deoxy compounds silyhermin A and B; 2,3 dehydrosilybin; and the trimers, quatramers and pentamers of silybin (which collectively are referred to as silybinomers). Other flavanolignans may be included as well. Isomers of silybin (or silybinin) are silybin A and B (or silybinin A and B). For purposes of this application, the term, "silybin" shall be used, but shall include silybinin. The structure of some of these are illustrated in: (FIG. 7). Tyler, V., The Honest Herbal, Haworth Press, Inc., New York, 1993, pp. 209–10; Wichtl, M. (Grainger Bisset, N, trans.), Herbal Drugs and Phytopharmaceuticals, CRC Press, Boca Raton, 1994, pp. 121, 124, 125. These hepatoprotectant flavonolignans are referred to in this application as "active components of silymarin." The fruits (often erroneously referred to as the "seeds") of the plant, for example, contain approximately 3% flavonolignans on average. Laboratory trials in animals have shown that silymarins protect liver tissue against a variety of toxins including those of the deadly amanita mushrooms and carbon tetrachloride. Prophylactic effects were especially pronounced. Milk thistle is usually available as an extract that contains silymarin, but it is envisioned that any form or formulation of Milk thistle, e.g., extract, precipitate, or powdered form, which contains either silymarin or one or more active components of silymarin, would function in the present invention. In a preferred embodiment of the invention, the Milk thistle component or components may be "standardized," i.e., formulated so that a certain percentage or amount of a specific substance or of specific substances is or are present. As an example, the Milk thistle component of the invention (i.e. silymarin and the principal active components of silymarin, such as silybin, silydianin and silychristin) could be an extract. In that case, the extract can be standardized with respect to the percentage by weight of any or all of the silymarin constituents, particularly the silybin fractions present in the extract. For example, silymarin may be present in the extract in an amount from about 55% to about 85% by weight of the extract. In a more preferred embodiment, silymarin may be standardized so that it is present in an amount from about 67.5% to about 72.5% by weight of the extract. In another preferred embodiment the extract can be standardized to the amount of Silybinin A and Silybinin B, which may be present in a combined amount from about 20% to about 35% by weight, and most preferably about 28% by weight of the extract. In a still further preferred embodiment, Isosilybin A (also known as Isosilybinin A) and Isosilybin B (also known as Isosilybinin B) may be present in a combined amount from about 20% to about 35% by weight of the extract, as measured by HPLC (high pressure liquid chromatography). It may be possible to standardize the extract with respect to other flavonolignan fractions or isomers, such as dehydrosilybin, silydianin and silycristin, as well as their 3-deoxy derivatives. Each of these preferred embodiments may be present alone or in any combination. Recently, it has been shown that oral absorption of silymarin can be increased by combining the silimarin with phosphatidylcholine and this combination may also be used in the present invention.

Silymarin and the active components of silymarin have several mechanisms of action, including stimulation of nucleolar polymerase A. This stimulation in turn increases ribosomal activity leading to increased synthesis of cellular proteins, and an increased rate of hepatocellular repair. Conti, M., et al., *Protective activity of Silipide on liver damage in rodents*, Japan J. Pharmacol., 60, 1992, pp. 315–21. Other protective mechanisms involve changes in the molecular structure of the hepatocellular membrane, which reduce binding and entry of toxins into the cell, and an antioxidant effect. Parish, R. & Doering, P., *Treatment of Amanita mushroom poisoning: a review*, Vet. Hum. Toxocol., 28 (4) 1986, pp. 318–22. It is expected that elements of the combinations of the present invention will work synergistically together because they have different, but complementary, mechanisms of action. Because liver diseases involve a complex interplay of numerous factors, the exact nature of which may remain obscure to the diagnosing clinician, there is a need for a composition that will address numerous mechanisms of liver damage. Treating the causative agent may not be—and in liver disease rarely is—possible. Addressing and preventing hepatic injuries on the cellular level therefore frequently will be the best treatment possible and almost as beneficial. The present invention combines antiinflammatory, anti-lipid, anti-necrotic, regenerating, and anti-fibrotic effects. All three ingredients that may be included in compositions of the present invention, S-adenosylmethionine, L-ergothioneine and a compound selected from the group consisting of Milk thistle, silymarin and active components of silymarin, have strong anti-inflammatory effects because of their antioxidant properties. Because different antioxidants have their primary effect on different free radicals, (for example, superoxide dismutase scavenges primarily superoxide anion), and because several types of free radicals are implicated in liver damage, supplying just one antioxidant would only address one subset of liver-damaging free radicals. It would also have a direct protective effect on protecting the hepatic cells when cells are stimulated by SAMe and or Silymarin to increase protein synthesis as this action of increased cell metabolism generates free radicals which can be neutralized by ergothionine.

Combining two of the three compounds will produce a beneficial effect in a number of liver diseases, and combining all three compounds will help treat or prevent an extremely broad range of such diseases. Thus, the compositions and combinations of the present invention will improve and maintain the health of liver tissue and normalize and improve the function of the liver in humans and animals. The combination will also allow beneficial effects to be achieved using lower doses than would otherwise be necessary. The use of lowered doses is both economically advantageous and reduces the risk of any potential side effects. Although the present ingredients are remarkably free of side effects, no compound is completely innocuous and giving the lowest effective dose is always sound medical policy.

The compositions and combinations of the present invention can be administered by a variety of routes including, but not limited to: orally, parentally, transdermally, sublingually, intravenously, intramuscularly, rectally and subcutaneously. Preferred daily doses for each of the compounds are as follows. As would be apparent to a person of ordinary skill in the art, these dose ranges are approximations:

SAMe

Total dose range: about 5 mg–about 10 grams

Preferred small animal dose range: about 5 mg–about 1600 mg

Preferred human dose range: about 20 mg–about 5000 mg

Preferred large animal dose range: about 100 mg–about 10 grams

Alternatively, the daily per kilogram dose range of SAMe for all species is: about 2 mg/kg–about 100 mg/kg L-ergothioneine Total dose range: about 5 $\mu$g–about 25 grams Preferred small animal dose range: about 5 $\mu$g–about 5 grams Preferred human dose range: about 25 $\mu$g–about 10 grams Preferred large animal dose range: about 100 $\mu$g–about 25 grams Alternatively, the daily per kilogram dose range of L-ergothionine for all species is: about 2 $\mu$g/kg–about 250 mg/kg Constituent of Milk thistle or Silymarin, or Active Components of Silymarin, (i.e., Silybin, Isosilybin, etc.)

Total dose range: about 5 mg–about 10 grams

Preferred small animal dose range: about 5 mg–about 1000 mg

Preferred human dose range: about 100 mg–about 5 grams

Preferred large animal dose range: about 250 mg–about 10 grams

Alternatively, the daily per kilogram dose range of a constituent of Milk thistle, silymarin, or active components of silymarin for all species is: about 1 mg/kg–about 200 mg/kg The daily doses recited above for all compounds may be given in a single dose or divided doses, to be administered, for example, twice-a-day, three-times a day or four-times-a-day. Therefore, the range for a single dose of the components of the invention is as follows:

SAMe

Total single dose range: about 1.25 mg–about 10 grams

Preferred small animal single dose range: about 1.25 mg–about 1600 mg

Preferred human single dose range: about 5 mg–about 5000 mg

Preferred large animal single dose range: about 25 mg–about 10 grams

Alternatively, the per kilogram single dose range of SAMe for all species is: about 0.5 mg/kg–about 100 mg/kg L-ergothioneine Total single dose range: about 1.25 μg–about 25 grams Preferred small animal single dose range: about 1.25 μg–about 5 grams Preferred human single dose range: about 6.25 μg–about 10 grams Preferred large animal single dose range: about 25 μg–about 25 grams Alternatively, the per kilogram single dose range for all species is: about 0.5 μg/kg–about 250 mg/kg Constituent of Milk Thistle
(or Silymarin, or Active Components of Silymarin, i.e., Silybin, Isosilybin, etc.)

Total single dose range: about 1.25 mg–about 10 grams

Preferred small animal single dose range: about 1.25 mg–about 1000 mg

Preferred human single dose range: about 25 mg–about 5 grams

Preferred large animal single dose range: about 62.5 mg–about 10 grams

Alternatively, the per kilogram single dose range of a constituent of Milk thistle, silymarin, or active components of silymarin for all species is: about 0.25 mg/kg–about 200 mg/kg Moreover, the dose may be administered in various combinations in which the components may be present in a single dosage form or in more than one dosage form. For example, the combinations of the present invention may be administered in a single daily dosage form in which all components are present, e.g., in a single capsule or tablet. The doses may also be administered in combinations of more than one dosage form in which each dosage form contains at least one component or in which two or more components are combined into a single dosage form. For example, a combination of SAMe and ergothioneine may be administered as a pill, capsule or tablet of SAMe and a separate pill, tablet or capsule of ergothioneine. A combination of ergothioneine, SAMe and silymarin may include each component in a separate dosage form, or two of the components in one dosage form, such as combined in the same capsule and the other component in a separate dosage form, or, as explained above, all three of the components in the same (i.e., a single) dosage form. These combinations may be provided in kits or blister packs, in which more than one dosage form of the various components are provided in the same package or container, for co-administration to a human or animal. For example, a tablet of SAMe and a capsule of silymarin can be placed in the same blister pack for co-administration. These combinations may be provided, for example, in kits, blister packs, packets or bottles shrink-wrapped together in which more than one dosage form of the various components are provided in the same dispensing unit for coadministration to a human or animal.

Having discussed the composition of the present invention, it will be more clearly perceived and better understood from the following specific examples which are intended to provide examples of the preferred embodiments and do not limit the present invention. Moreover, as stated above, the preferred components described in these examples may be replaced by or supplemented with the any of the components of the compositions of the invention described above.

EXAMPLE 1

A 10-year-old female spayed domestic cat is diagnosed with feline idiopathic hepatic lipidosis (fatty liver). This disease is characterized by the accumulation of triglycerides within the cytoplasm of liver cells. The cells become so swollen with lipids that they cease to function, and many die (hepatic necrosis). The cellular swelling also inhibits blood flow in hepatic sinusoids, compounding the damage with poor perfusion. Symptoms of the disease include loss of appetite, vomiting, depression and CNS signs (hepatic encephalopathy). Since the cause of this disease is unknown, it is currently treated symptomatically. Even with aggressive treatment, 40 to 50% of affected animals succumb. In this case, in addition to symptomatic treatment (tube feeding, fluids, pharmacologic control of vomiting), the patient is given daily a mixture of 100 mg SAMe, 100 mg silymarin, and 100 mg of L-ergothionine until appetite returns. The SAMe and silymarin support repair of damaged hepatocytes and their function, the production of enzymes and other proteins. The L-ergothioneine prevents reperfusion injury. The net result is that the cat recovers, and the rate of recovery is increased so that the cat spends fewer days hospitalized.

EXAMPLE 2

A farmer in Lancaster County, Pa., reports that one of his cows has died in convulsions and that several sheep and a pig in the same pasture are also sick. Poisoning by cocklebur plants (*Xanthium strumarium*) is diagnosed. In this condition, a toxin produced by the plant causes fatty change, swelling, and death in liver cells. Animals that survive the initial illness may develop chronic liver disease. Currently, the only method of treatment is removal of the plant from the diet. In this case, the pigs and sheep are removed from the pasture and administered daily SAMe (5 mg/kg), silymarin (40 mg/kg), and L-ergothioneine (100 mg per animal) for one to two weeks. The SAMe helps maintain cellular membranes and the Na/K/ATPase pump, which are the cellular organelles most likely to be damaged by the toxin. The silymarin stimulates synthesis of replacement proteins and the L-ergothioneine prevents reperfusion injury.

EXAMPLE 3

A 58-year-old man has osteoarthritis. To control the pain in his joints, he takes large amounts of the drug acetaminophen. Like many other drugs, acetaminophen can cause hepatic damage by decreasing glutathione levels. This patient wishes to continue to take acetaminophen, because nonsteroidal anti-inflammatory drugs cause unacceptable gastrointestinal irritation. In this case, the patient continues to take acetaminophen, but also takes SAMe 200 mg, and L-ergothioneine 100 mg daily as long as he continues to take acetaminophen. The SAMe increases hepatic glutathione levels, and the L-ergothioneine ensures maximum effect of the available glutathione via glutathione peroxidase activation. The net result is that liver structure and function are supported in the face of an ongoing potentially hepatotoxic exposure.

Many modifications may be made without departing from the basic spirit of the present invention. Accordingly, it will be appreciated by those skilled in the art that within the scope of the appended claims, the invention may be practiced other than has been specifically described herein. Hence, the attached claims are intended to cover the invention embodied in the claims and substantial equivalents thereto.

We claim:

1. A composition comprising:
   a first component comprising S-adenosylmethionine; and
   a second component comprising at least one substance selected from the group consisting of L-ergothioneine and a milk thistle component.

2. The composition of claim 1, wherein the milk thistle component comprises one or more substances selected from the group consisting of Milk thistle (*Silybum marianum*) a constituent of Milk thistle (*Silybum marianum*), silymarin and active components of silymarin.

3. The composition of claim 1, wherein a single dose of S-adenosylmethionine ranges from about 1.25 milligrams to about 10 grams.

4. The composition of claim 1, wherein a single dose of S-adenosylmethionine ranges from about 0.5 milligrams per kilogram to about 100 milligrams per kilogram.

5. The composition of claim 1, wherein a single dose of L-ergothioneine ranges from about 1.25 micrograms to about 25 grams.

6. The composition of claim 1, wherein a single dose of L-ergothioneine ranges from about 0.5 micrograms per kilogram to about 250 milligrams per kilogram.

7. The composition of claim 1, wherein a single dose of the milk thistle component ranges from about 1.25 milligrams to about 10 grams.

8. The composition of claim 1, wherein a single dose of the milk thistle component ranges from about 0.25 milligrams per kilogram to about 200 milligrams per kilogram.

9. The composition of claim 1, wherein the milk thistle component is standardized such that silymarin is present in that component in an amount from about 55% to about 85% by weight of that component.

10. The composition of claim 9, wherein silymarin is present in the milk thistle component in an amount from about 67.5% to about 72.5% by weight of that component.

11. The composition of claim 1, wherein the milk thistle component is standardized such that Silybin A and Silybin B are present in that component in a combined amount from about 20% to about 35% by weight of that component.

12. The composition of claim 11, wherein Silybin A and Silybin B are present in the milk thistle component in a combined amount of about 28% by weight of that component.

13. The composition of claim 1, wherein the milk thistle component is standardized such that Isosilybin A and Isosilybin B are present in that component in a combined amount from about 20% to about 35% by weight of that component.

14. A method of improving or maintaining the health of liver tissue or of normalizing or improving the function of the liver comprising:
    administering a therapeutically or prophylactically effective amount of the composition of claim 1.

15. The method of claim 14, wherein the milk thistle component comprises one or more substances selected from the group consisting Milk thistle (*Silybum marianum*), a constituent of Milk thistle (*Silybum marianum*), silymarin and active components of silymarin.

16. The method of claim 14 wherein a daily dose of S-adenosylmethionine ranges from about 5 milligrams to about 10 grams.

17. The method of claim 14 wherein a daily dose of S-adenosylmethionine ranges from about 2 milligrams per kilogram to about 100 kilogram.

18. The method of claim 14 wherein a daily dose of L-ergothioneine ranges from about 5 micrograms to about 25 grams.

19. The method of claim 14 wherein a daily dose of L-ergothioneine ranges from about 2 micrograms per kilogram to about 250 milligrams per kilogram.

20. The method of claim 14 wherein a daily dose of the milk thistle component ranges from about 5 milligrams to about 10 grams.

21. The method of claim 14 wherein a daily dose of the milk thistle component ranges from about 1 milligram per kilogram to about 200 milligrams per kilogram.

22. A kit comprising:
    a first component comprising S-adenosylmethionine; and
    a second component comprising at least one substance selected from the group consisting of L-ergothioneine and a milk thistle component,
    wherein each of the first and second components is provided in a separate dosage form, and, if both L-ergothioneine and the milk thistle component are present in the kit, they are provided either in seperate dosage forms or together in a single dosage form; and
    wherein said kit is assembled such that the dosage forms for the first and second components are provided in a package.

23. The kit of claim 22, wherein the milk thistle component comprises one or more substances selected from the group consisting of Milk thistle (*Silibym marianum*), a constituent of Milk thistle (*Silybum marianum*), silymarin and of silymarin.

24. The kit of claim 22, wherein a single dose of S-adenosylmethionine ranges from about 1.25 milligrams to about 10 grams.

25. The kit of claim 22, wherein a single dose of S-adenosylmethionine ranges from about 0.5 milligrams per kilogram to about 100 kilogram.

26. The kit of claim 22, wherein a single dose of L-ergothioneine ranges from about 1.25 micrograms to about 25 grams.

27. The kit of claim 22, wherein a single dose of L-ergothioneine ranges from about 0.5 micrograms per kilogram to about 250 milligrams per kilogram.

28. The kit of claim 22, wherein a single dose of the milk thistle component ranges from about 1.25 milligrams to about 10 grams.

29. The kit of claim 22, wherein a single dose of the milk thistle component ranges from about 0.25 milligrams per kilogram to about 200 milligrams per kilogram.

30. The kit of claim 22, wherein the milk thistle component is standardized such that silymarin is present in that component in an amount from about 55% to about 85% by weight of that component.

31. The kit of claim 30, wherein silymarin is present in the milk thistle component in an amount from about 67.5% to about 72.5% by weight of that component.

32. The kit of claim 22, wherein the milk thistle component is standardized such that Silybin A and Silybin B are present in that component in a combined amount from about 20% to about 35% by weight of that component.

33. The kit of claim 32, wherein Silybin A and Silybin B are present in the milk thistle component in a combined amount of about 28% by weight of that component.

34. The kit of claim 22, wherein the milk thistle component is standardized such that Isosilybin A and Isosilybin B are present in that component in a combined amount from about 20% to about 35% by weight of that component.

35. A method of improving or maintaining the health of liver tissue or of normalizing or improving the function of the liver comprising:
    administering a therapeutically or prophylactically effective amount of the components of the kit of claim 22.

36. The method of claim 35, wherein the milk thistle component comprises one or more substances selected from the group consisting Mik thistle (*Silybum marianum*), a constituent of Milk thistle (*Silybum marianum*), silymarin and active components of silymarin.

37. The method of claim 35 wherein a daily dose of S-adenosylmethionine ranges from about 5 milligrams to about 10 grams.

38. The method of claim 35 wherein a daily dose of S-adenosylmethionine ranges from about 2 milligrams per kilogram to about 100 kilogram.

39. The method of claim 35 wherein a daily dose of L-ergothioneine ranges from about 5 micrograms to about 25 grams.

40. The method of claim 35 wherein a daily dose of L-ergothioneine ranges from about 2 micrograms per kilogram to about 250 milligrams per kilogram.

41. The method of claim 35 wherein a daily dose of the milk thistle component ranges from about 5 milligrams to about 10 grams.

42. The method of claim 35 wherein a daily dose of the milk thistle component ranges from about 1 milligram per kilogram to about 200 milligrams per kilogram.

43. The kit of claim 22 wherein the package is selected from the group consisting of:

a carton, a dispensing unit and a shrink-wrapped assembly of two or more containers.

44. The kit of claim 22, wherein the kit comprises one or more sheets of blister packs comprising dosage forms of the first component and one or more sheets of blister packs comprising dosage forms of the second component.

45. The kit of claim 22, wherein the kit comprises a plurality of sheets of blister packs, wherein each sheet comprises at least one blister pack comprising the dosage form of the first component and at least one blister pack comprising the dosage form of the second component.

46. The kit of any of claims 22, 44, or 45, wherein the dosage form for each of the first and second components is selected from the group consisting of a pill, a tablet, a capsule, and another acceptable oral dosage form.

47. The kit of any one of claims 44 or 45, wherein the first component is S-adenosylmethionine and the second component is the milk thistle component comprises one or more substances selected from the group consisting of Milk thistle (*Silybum marianum*), a constituent of Milk thistle (*Silybum marianum*), silymarin and active components of silymarin.

48. The kit of any of claims 44 or 45, wherein the first component is S-adenosylmethionine and the second component is L-ergothioneine.

49. The kit of any of claims 44 or 45, wherein the first component is S-adenosylmethionine and the second component comprises L-ergothioneine and the milk thistle component, wherein the milk thistle component comprises one or more substances selected from the group consisting of Milk thistle (*Silybum marianum*), a constituent of Milk thistle (*Silybum marianum*), silymarin and active components of silymarin.

* * * * *

UNITED STATES PATENT AND TRADEMARK OFFICE
CERTIFICATE OF CORRECTION

PATENT NO.       : 6,863,906 B2
APPLICATION NO. : 10/153877
DATED            : March 8, 2005
INVENTOR(S)      : Todd R. Henderson et al.

It is certified that error appears in the above-identified patent and that said Letters Patent is hereby corrected as shown below:

In the Claims:

Col. 11, line 64, "100 kilogram" should be changed to --100 milligrams per kilogram--.

Col. 12, line 18, "seperate" should be changed to --separate--;

Col. 12, line 26, "and of silymarin" should be changed to --and active components of silymarin--.

Col. 12, line 32, "100 kilogram" should be changed to --100 milligrams per kilogram--.

Col. 13, line 11, "100 kilogram" should be changed to --100 milligrams per kilogram--.

Col. 14, line 13, "component comprises" should be changed to --component, wherein the milk thistle component comprises--.

Signed and Sealed this

First Day of May, 2007

JON W. DUDAS
*Director of the United States Patent and Trademark Office*